(12) United States Patent
Ricks-Laskoski et al.

(10) Patent No.: US 9,217,062 B2
(45) Date of Patent: Dec. 22, 2015

(54) C-SUBSTITUTED, 1H-AZOLES FOR AMPHOTERIC, SOLVENT-LESS PROTON CONDUCTIVITY

(71) Applicants: Holly L. Ricks-Laskoski, Springfield, VA (US); Arthur W Snow, Alexandria, VA (US); Matthew Laskoski, Springfield, VA (US); Stephen M. Deese, Burke, VA (US); Brian L. Chaloux, Alexandria, VA (US)

(72) Inventors: Holly L. Ricks-Laskoski, Springfield, VA (US); Arthur W Snow, Alexandria, VA (US); Matthew Laskoski, Springfield, VA (US); Stephen M. Deese, Burke, VA (US); Brian L. Chaloux, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 89 days.

(21) Appl. No.: 13/957,391

(22) Filed: Aug. 1, 2013

(65) Prior Publication Data

US 2014/0039132 A1 Feb. 6, 2014

Related U.S. Application Data

(60) Provisional application No. 61/678,749, filed on Aug. 2, 2012.

(51) Int. Cl.
*C08G 75/00* (2006.01)
*C08G 65/00* (2006.01)
*C07D 257/04* (2006.01)
*C08G 73/06* (2006.01)
*C08G 67/02* (2006.01)

(52) U.S. Cl.
CPC .......... *C08G 73/0605* (2013.01); *C07D 257/04* (2013.01); *C08G 65/002* (2013.01)

(58) Field of Classification Search
USPC ........................................................ 528/390
See application file for complete search history.

(56) References Cited

PUBLICATIONS

Huber et al. "Complexation of Unsaturated Carbon-Carbon Bonds in δ -Conjugated Polymers with Transition Metals" J. Am. Chem. Soc. 2001, 123, volumer 123 No. 173857-3863; DAS.*

*Primary Examiner* — Terressa Boykin
(74) *Attorney, Agent, or Firm* — US Naval Research Laboratory; Rebecca L. Forman

(57) ABSTRACT

Disclosed herein are the compounds shown below. Also disclosed are methods of making the compounds.

$R_1$=—O—;

$R_2$=any alkyl chain;

$R_3$=—$CH_3$, —CN, —$COOCH_3$, -tetrazole, -imidazole, or -triazole;

$R_4$=—H or —$R_5$;

$R_5$=—H, -halogen, —C≡CH, or —C≡C—;

n is a positive integer; and m is a positive integer.

8 Claims, 6 Drawing Sheets

random coil
with pendent
tetrazoles (b)

C-SUBSTITUTED, 1H-AZOLES FOR AMPHOTERIC, SOLVENT-LESS PROTON CONDUCTIVITY

PRIORITY CLAIM

This application claims priority from U.S. Provisional Application No. 61/678,749 filed on Aug. 2, 2012 by Holly L. Ricks-Laskoski et al., entitled "C-Substituted, 1H-Azoles for Amphoteric, Solvent-less Proton Conductivity." The provisional application and all other publications and patent documents referred to throughout this nonprovisional application are incorporated herein by reference.

BACKGROUND OF THE INVENTION

1. Field of the Invention

The present invention relates generally to polymers with pendent 1H-azoles and more specifically to c-substituted, 1H-azoles for amphoteric, solvent-less proton conductivity.

2. Description of the Prior Art

The search for efficient/alternative fuel sources has opened many opportunities for the development of both known and new materials. Nafion, for example, is a polymeric material first synthesized in the late 1960's that is used as the proton exchange membrane (PEM) in hydrogen fuel cells of today. The chemical composition of Nafion shows a morphology consisting of both hydrophobic and hydrophilic sites where upon hydration forms channels in which movement of cations, specifically the hydrogen cation or proton, hop from one hydrophilic site to another but does not permit the passage of anions or electrons. This "hopping" mechanism is called the Grotthus mechanism.

Rapid proton transport in water by both structural and vehicular motion of protic defects in the hydrogen bonded network is well known. Many applications currently rely on the high conductivity of aqueous systems, with fuel cell membranes among them. However, other amphoteric molecules, those capable of acting simultaneously as a Brønsted acid (proton donor) and base (proton acceptor), have also been shown to exhibit proton transport by similar means. (A. Kawada et al., *J. Chem. Phys.*, 52 (6), 3121-25 (1970)). Many recent materials designed for anhydrous proton transport belong to the azole family of amphoteric, five-membered heterocycles, and several interesting synthetic strategies have been developed to allow access to azoles that retain an intact NH proton. (J. C. Loren et al., *Synlett*, 18, 2847-50 (2005); Z. P. Demko et al., *J. Org. Chem.*, 66, 7945-50 (2001); V. Aureggi et al., *Angew. Chem. Int. Ed.*, 46, 8440-44 (2007); S. Martwiset et al., *Solid State Ionics*, 178, 1398-1403 (2007)). Among these materials, triazoles and imidazoles have been widely studied as plasticizers to polyacids and pendant moieties within polymer matrices.

Substituted tetrazoles are a unique class of heterocycles with a wide range of potential applications ranging from coordination to medicinal chemistry and many uses in material science. (P. Lin et al., *Dalton Trans.* 2388 (2005); A. K. Gupta et al., *Synlett*, 12, 2227 (2004); E. H. White et al., *Tetrahedron Lett.*, 21, 758 (1961); H. Zue, *Chem. Mater.* 17, 19 (2005)). These compounds are usually obtained by the addition of azide salts to nitriles under heating conditions. (S. J. Wittenberger, *J. Org. Prep. Proced. Intl.* 26, 499 (1994); B. E. Huff et al., *Tetrahedron Lett.*, 34, 8011 (1993); J. Sauer et al., *Tetrahedron*, 11, 241 (1960)). These procedures have been known since the 1930s, often employing toxic metals, expensive reagents and harsh reaction conditions. Moreover, the resulting compounds proved difficult to isolate from the resulting reaction side-products. In 2007, a simplified synthetic procedure was described by Aureggi et al. for the synthesis of 5-substituted tetrazoles using click chemistry. (V. Aureggi et al., *Angew. Chem. Int. Ed.*, 46, 8440-44 (2007)). By reacting organoaluminum azides with a variety of functionalized nitriles, a range of molecules containing a pendent tetrazole were described.

The weakly acidic 1H-tetrazole is an understudied member of the azole family with respect to materials applications. The majority of research on this four-nitrogen, one-carbon azole has been on its pharmacological applications as a carboxylic acid congener. To date, 1H-tetrazole-bearing polymers appear to be unexplored for ion exchange membrane applications, despite prior observation of their potential utility in this area. (N. V. Tsarevski et al., *Macromolecules*, 37, 9308-9313 (2004)). Tetrazole-bearing polymers have traditionally been polymerized from tetrazole-bearing vinyl monomers or converted post-polymerization from acrylo- or aryl-nitriles in dimethylformamide (DMF) by action of either hydrazoic acid, generated in situ, or azide anion, catalyzed by zinc salts. (V. V. Annenkov et al., *J. Polym. Sci., Part A: Polym. Chem.*, 31, 1903-06 (1993); A. Taden et al., *J. Polym. Sci., Part A: Polym. Chem.*, 40, 4333-43 (2002); V. N. Kizhnyaev et al., *Russ. Chem. Rev.*, 72 (2), 143-164 (2003); P. N. Gaponik et al., *Angew. Makromol. Chem.*, 219, 77-88 (1994); M. R. Huang et al., *React. Funct. Polym.*, 59, 53-61 (2004); N. Du et al., *Nat. Mat.*, 10, 372-75 (2011); N. Du et al., *Polymer*, 53, 4367-4372 (2012)).

BRIEF SUMMARY OF THE INVENTION

The present invention provides a rigid rod and random coil polymer with pendent 1H-azoles. These polymers are prepared with the azole acting as an amphoteric moiety when in a water-free environment. The synthesis of a rigid-rod trimer and random coil polymer with pendent 1H-tetrazoles are described in detail.

The present invention provides a general procedure for the high-yield synthesis of polymeric 1H-tetrazoles using low temperatures, low polarity solvents, and forgoing potentially explosive and acutely toxic intermediates (e.g. $NH_4N_3$). Some advantages of this method are that it utilizes safe and effective techniques and is scalable to large quantities. Because of the presence of the pendent tetrazole molecule, the polymers of this invention are expected to show high conductivity with little to no humidity.

These and other features and advantages of the invention, as well as the invention itself, will become better understood by reference to the following detailed description, appended claims, and accompanying drawings.

DETAILED DESCRIPTION OF THE INVENTION

Figure 1:
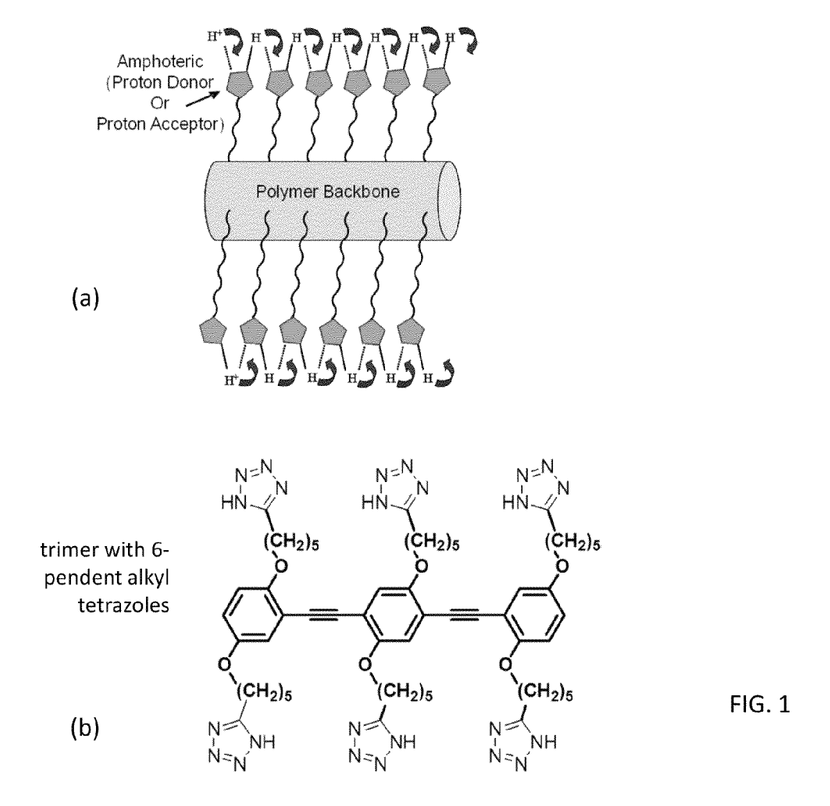
FIG. 1 shows (a) a schematic of a rigid-rod polymer backbone with amphoteric moieties attached and (b) the chemical structure of a trimer with 6-pendent alkyl tetrazoles.
Figure 2:
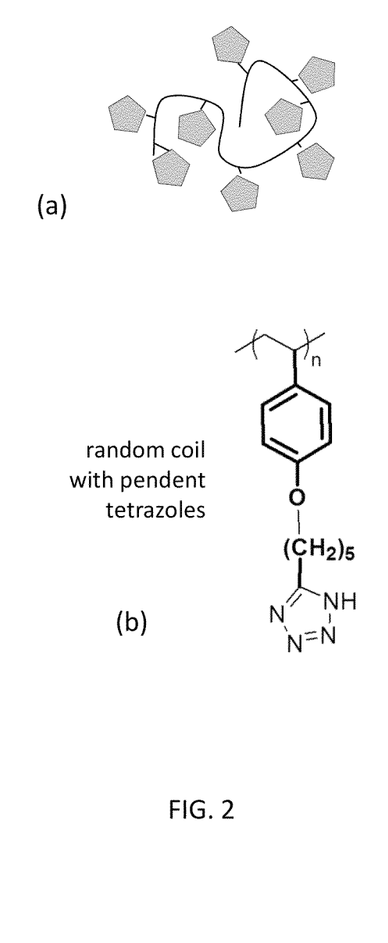
FIG. 2 shows (a) a schematic of a random coil polymer and (b) the chemical structure of the random coil with pendent tetrazoles.

The present invention provides for the synthesis of rigid-rod (see FIG. 1) and random coil polymers (see FIG. 2) with pendent 1H-tetrazoles in the absence of water. The anhydrous proton conductivity of these molecules takes advantage of the amphoteric nature of the N-rich heterocyclic side chains.

1H-tetrazole was chosen to act as the "amphoteric moiety" in a water-free environment. Consisting of 4 nitrogen atoms and one carbon atom, of all the azoles tetrazole has the lowest pka of 4.9. Ease of protonation and deprotonation is attractive for proton conduction. Tethering tetrazole through its only carbon ensures the freedom of the four nitrogen atoms to donate or accept protons from neighboring pendent tetrazoles, setting up a greater chance of recreating the Grotthus mechanism.

For one embodiment of the invention, to ensure hopping between pendent neighbors, a rigid-rod backbone such as poly(phenylene ethynylene) (PPE) was used as the supporting structure for proton conduction. Unlike Nafion which depends on its morphology and hydration to achieve high proton conductivity, the present invention relies on molecular design to ensure proton conduction similar to a proton hopping mechanism.

Reagents.

All reagents were purchased from the Aldrich Chemical Co. and used without further purification unless otherwise noted.

Azide Handling and Quenching.

Precautions were taken when handling azides to forbid exposure to metals, possible shock sensitivities, and the hydrolysis product hydrozoic acid. Under argon and at a temperature of 0° C., all azide reactions were quenched first with NaOH/NaNO$_2$ (3.7 M) until a pH of 11 was reached followed by the addition of 6M HCl until a pH of 3 to ensure safe destruction of any unreacted azide and liberate the intact tetrazole and water soluble aluminum salts. This method insured the safest destruction of unreacted azide via solution under an inert atmosphere.

Instrumentation.

All $^1$H-HMR spectroscopy were obtained using a Bruker AC-300 spectrometer using d$_6$-DMSO, CDCl$_3$, or d$_6$-acetone as solvent.

(2)

9917-64

Figure 3:
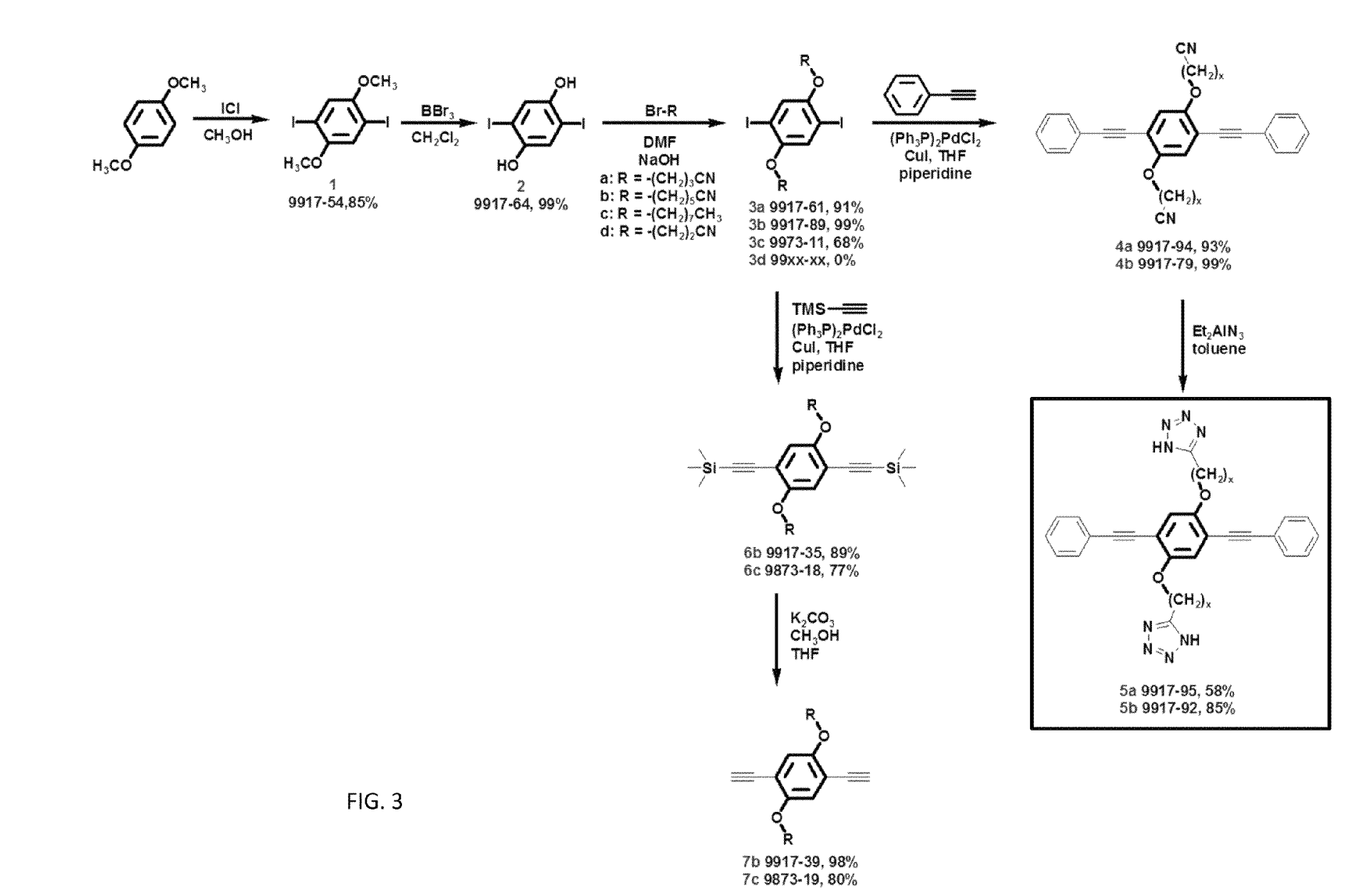
FIG. 3 shows a reaction schematic to form a PPE trimer with two tetrazoles.

Synthesis of 2,5-diiodohydroquinone (2)
(See FIG. 3)

Following a previously published preparation (K. Wariishi et al., Organic Process Research & Development, 7, 29-100 (2003)), a nitrogen purged 500 ml three-neck flask was charged with diiododimethoxy benzene (1) (49.42 g, 126.7 mmol) and stirred until dissolved in methylene chloride (200 ml). The reaction flask was cooled (dry ice/ethanol) and boron tribromide (127 g, 506.9 mmol) was added slowly via an addition funnel with the reaction flask vented to a bubblier. The reaction mixture warmed to room temperature and reacted for 17 hr. The pale pink reaction mixture was carefully quenched by pouring into 1 L of chilled water. The white precipitant was collected via suction filtration, washed with excess water until neutral, and dried under vacuum to yield 2 (45.86 g, 99%) which was used without further purification. $^1$H NMR (300 MHz, CDCl$_3$): δ 7.27 (s, 2H), 5.13 (s, 2H). $^{13}$C NMR (60 MHz, acetone-d$_6$): δ 150.75, 124.06, 83.51.

(3)

9917-61 (R=—(CH$_2$)$_3$CN), 9917-89 (R=—(CH$_2$)$_5$CN), 9873-11 (R=—(CH$_2$)$_7$CH$_3$)

Synthesis of Diiododialkyoxynitrile Benzene (3)
(See FIG. 3)

To a 500 ml schlenk flask under argon fitted with a stir bar was added 2 (1 eq.), the selected bromoalkylnitrile or bromoalkane (2.02 eq.), and anhydrous DMF (0.3 M). This mixture was deoxygenated via the freeze-pump-thaw method (3 times) then backfilled with argon. Freshly ground sodium hydroxide (6.63 g, 166 mmol) was added and the reaction was stirred at room temperature for 18 hr or until complete as indicated by TLC (SiO$_2$: R$_f$=0.4, 30% ethyl acetate/hexanes). The crude reaction mixture was precipitated into 1M HCl, filtered via suction filtration, and dried under vacuum to yield 3 as a light tan powder which was used without further purification.

3a, whereby R=—(CH$_2$)$_3$CN: The reagents used: 2 (10.00 g, 27.6 mmol) and 4-bromobutyronitrile (8.26 g, 55.8 mmol) yielded 3a (12.48 g, 91%). $^1$H NMR (300 MHz, CDCl$_3$): δ 7.17 (s, 2H), 4.04 (t, 4H, J=5.58 Hz), 2.68 (t, 4H, J=7.10 Hz), 2.15 (q, 4H, J=5.82 Hz). $^{13}$C NMR (60 MHz, CDCl$_3$): δ 152.44, 122.87, 119.01, 86.23, 67.47, 25.43, 14.33.

3b, whereby R=—(CH$_2$)$_5$CN: The reagents used: 2 (15.00 g, 41.4 mmol) and 6-bromohexanenitrile (14.74 g, 83.7 mmol) yielded 3b (22.5 g, 99%). $^1$H NMR (300 MHz, CDCl$_3$): δ 7.14 (s, 2H), 3.93 (t, 4H, J=5.91 Hz), 2.38 (t, 4H, J=6.67 Hz), 1.83-1.65 (m, 12H). $^{13}$C NMR (60 MHz, CDCl$_3$): δ 152.73, 122.75, 119.54, 86.21, 69.65, 28.27, 25.46, 25.09, 17.16.

3c, whereby R=—(CH$_2$)$_7$CH$_3$: The reagents used: 2 (5.00 g, 13.8 mmol) and 8-bromooctane (5.39 g, 27.9 mmol) yielded 3c (5.54 g, 68%). $^1$H NMR (300 MHz, CDCl$_3$): δ 7.15 (s, 2H), 3.90 (t, 4H, J=6.41 Hz), 1.76 (q, 4H, J=6.44 Hz), 1.49-1.42 (m, 4H), 1.29-1.27 (m, 16H), 0.88 (t, 6H, J=6.64 Hz). $^{13}$C NMR (60 MHz, CDCl$_3$): δ 152.77, 122.67, 86.25, 70.27, 31.78, 29.22, 29.20, 29.11, 26.00, 22.65, 14.12.

(4)

9917-94 (R=—(CH$_2$)$_3$CN), 9917-79 (R=—(CH$_2$)$_5$CN)

(5)

9917-95 (R=—(CH$_2$)$_3$CN), 9917-92 (R=—(CH$_2$)$_5$CN)

Synthesis of PPE Trimer with Two Nitriles (4) (See FIG. 3)

Under argon, a 250 ml schlenk flask fitted with a stir bar was charged with 3 (1 eq.), bis(triphenylphosphine)palladium(II) dichloride (2 mol %), copper(I) iodide (1 mol %), piperidine (0.7 M), and tetrahydrofuran (1.8 M) as a co-solvent. The reaction flask was then deoxygenated via the freeze-pump-thaw method (3 times), backfilled with argon, and gently heated with a heat gun until a homogeneous mixture was observed. Phenylacetylene (2.3 eq.) was syringed into the flask at which time the reaction mixture became heterogeneous and exothermic. After stirring at room temperature for 18 hr, the now solidified yellow reaction mixture was quenched with 6 M HCl until acidic, filtered via suction filtration, and washed with excess water until neutral. The crude material was then dissolved in methylene chloride and recrystallized from ethanol, filtered via suction filtration and dried under vacuum to give 4 as yellowish-brown crystals. If further purification was required, flash chromatography (SiO$_2$: 30% ethyl acetate/hexanes) was performed.

4a, whereby R=—(CH$_2$)$_3$CN: The reagents used: 3a (5.00 g, 10.1 mmol) and phenylacetylene (2.37 g, 23.2 mmol), yielded 4a (4.17 g, 93%). $^1$H NMR (300 MHz, CDCl$_3$): δ 7.52-7.38 (m, 4H), 7.37-7.33 (m, 6H), 7.02 (s, 2H), 4.15 (t, 4H, J=5.66 Hz), 2.68 (t, 4H, J=7.16 Hz), 2.19 (q, 4H, J=5.68 Hz). $^{13}$C NMR (60 MHz, CDCl$_3$): δ 153.10, 131.43, 128.58, 128.45, 122.91, 119.10, 117.38, 114.34, 95.34, 85.09, 66.96, 25.57, 13.98.

4b, whereby R=—(CH$_2$)$_5$CN: The reagents used: 3b (5.34 g, 9.67 mmol) and phenylacetylene (2.07 g, 20.3 mmol), yielded 4b (4.81 g, 99%). $^1$H NMR (300 MHz, CDCl$_3$): δ 7.54-7.49 (m, 4H), 7.40-7.32 (m, 4H), 7.00 (s, 2H), 4.04 (t, 4H, J=6.05 Hz), 2.30 (t, 4H, J=6.83 Hz), 1.89-1.66 (m, 12H). $^{13}$C NMR (60 MHz, CDCl$_3$): δ 153.45, 131.45, 128.43, 128.40, 123.19, 119.57, 117.05, 114.05, 94.93, 85.66, 69.06, 28.34, 25.44, 25.15, 17.05.

Synthesis of PPE Trimer with Two Tetrazoles (5) (See FIG. 3)

Using glove box techniques, a 200 ml schlenk flask fitted with a stir bar was charged with diethylaluminum chloride (25 wt. % in toluene). The sealed schlenk flask was taken out of the glovebox, attached to a schlenk line under argon, and chilled to 0° C. Sodium azide (1 eq.) was then added to the reaction flask, warmed to room temperature, and stirred for 4 hr which produced a cloudy-white mixture. A separate 100 ml schlenk flask under argon also fitted with a stir bar was charged with 4 (1:6, ratio of compound 4 to Et$_2$AlN$_3$) and anhydrous toluene (40 mM) and/or 1-chlorobenzene or 1,2-dichlorobenzene as co-solvent deoxygenated via the freeze-pump-thaw method (3 times), and backfilled with argon. The diethylaluminum azide mixture was again chilled to 0° C. and the solution containing compound 4 was slowly added via syringe. The ice bath was removed, reaction flask sealed, and stirred at 110° C. for 18 hr. The reaction flask containing the crude reaction mixture was chilled to 0° C., opened to a schlenk line under argon fitted with a bubblier while a NaOH/NaNO$_2$ solution (3.7 M) was added until a pH of 11 was reached. To this mixture was then added 6 M HCl until a pH of 3 and the product obtained either by suction filtration or extraction with ethyl acetate and washed with excess water. The product was then dried under vacuum and stored in a desiccator to give 5 as a dark brown powder.

5a, whereby R=—(CH$_2$)$_3$CN: The reagents used: diethylaluminum chloride (6.52 ml, 12.0 mmol), sodium azide (0.78 g, 12.0 mmol), and 4a (1.00 g, 2.25 mmol) yielded 5a (0.69 g, 58%). $^1$H NMR (300 MHz, DMSO-d$_6$): δ 16.01 (bs, 2H-tetrazole), 7.55-7.52 (m, 4H), 7.45-7.40 (m, 6H), 7.21 (s, 2H), 4.14 (t, 4H, J=6.13 Hz), 3.13 (t, 4H, J=7.62 Hz), 2.25-2.16 (m, 4H). $^{13}$C NMR (60 MHz, 318 K, DMSO-d$_6$): δ 156.26, 153.60, 132.09, 131.73, 129.19, 123.03, 117.71, 11413, 95.42, 86.39, 68.58, 27.33, 20.10.

5b, whereby R=—(CH$_2$)$_5$CN: The reagents used: diethylaluminum chloride (5.43 ml, 10.0 mmol), sodium azide (0.65 g, 10.0 mmol), and 4b (1.00 g, 2.00 mmol) yielded 5b (1.00 g, 85%). $^1$H NMR (300 MHz, DMSO-d$_6$): δ 14.75 (bs, 2H-tetrazole), 7.57-7.47 (m, 4H), 7.45-7.40 (m, 6H), 7.13 (s, 2H), 4.11 (t, 4H, J=6.02 Hz), 3.01 (t, 4H, J=7.52 Hz), 1.98-1.86 (m, 8H), 1.82-1.62 (m, 4H). $^{13}$C NMR (60 MHz, DMSO-d$_6$): δ

155.91, 153.06, 131.17, 128.86, 128.76, 122.50, 116.57, 113.13, 94.72, 86.09, 68.64, 28.29, 26.79, 25.01, 22.75.

(6)

9917-35 (R=—(CH$_2$)$_5$CN), 9873-18 (R=—(CH$_2$)$_7$CH$_3$)

Alkyne Coupling Reaction (6) (See FIG. 3).

Under argon, a 250 ml schlenk flask fitted with a stir bar was charged with 3 (1 eq.), bis(triphenylphosphine)palladium(II) dichloride (2 mol %), copper(I) iodide (1 mol %), piperidine (0.7 M), and tetrahydrofuran (1.8 M) as co-solvent. The reaction flask was then deoxygenated via the freeze-pump-thaw method (3 times), backfilled with argon, and gently heated with a heat gun until a homogeneous mixture was observed. Trimethylsilylacetylene (2.1 eq.) was syringed into the flask at which time the reaction mixture became heterogeneous and exothermic. After stirring at room temperature for 18 hr or until completion as indicated by TLC (SiO$_2$: R$_f$=0.4, 30% ethyl acetate/hexanes). The dark-brown reaction mixture was filtered thru a short silica plug with ethyl acetate, concentrated by rotary evaporation, extracted into ethyl acetate, washed with 1 M HCl and water until neutral, dried over MgSO$_4$, filtered, and then concentrated by rotary evaporation. This crude material was recrystallized from ethanol or isopropanol, filtered via suction filtration and dried under vacuum to give 6 as slightly yellowish crystals.

6b, whereby R=—(CH$_2$)$_5$CN: The reagents used: 3b (5.00 g, 9.05 mmol) and trimethylsilylacetylene (1.87 g, 19.0 mmol), yielded 6b (3.69 g, 89%). $^1$H NMR (300 MHz, CDCl$_3$): δ 6.86 (s, 2H), 3.94 (t, 4H, J=5.98 Hz), 2.36 (t, 4H, J=6.94 Hz), 1.82-1.68 (m, 12H), 0.23 (t, 18H, J=3.50 Hz). $^{13}$C NMR (60 MHz, CDCl$_3$): δ 153.71, 119.59, 117.18, 113.90, 100.78, 100.34, 77.20, 68.71, 28.37, 25.38, 25.16, 17.14, 0.05.

6c, whereby R=—(CH$_2$)$_7$CH$_3$: The reagents used: 3c (1.00 g, 1.71 mmol) and trimethylsilylacetylene (0.35 g, 3.58 mmol), yielded 6c (0.69 g, 77%). $^1$H NMR (300 MHz, CDCl$_3$): δ 6.87 (s, 2H), 3.92 (t, 4H, J=6.20 Hz), 1.76-1.74 (m, 4H), 1.47-1.26 (m, 20H), 0.86-0.84 (m, 6H), 0.23 (s, 18H). $^{13}$C NMR (60 MHz, CDCl$_3$): δ 154.01, 117.20, 113.94, 101.07, 100.07, 69.45, 31.85, 29.40, 29.35, 29.30, 26.03, 22.67, 14.09, 0.25.

(7)

9917-39 (R=—(CH$_2$)$_5$CN), 9873-19 (R=—(CH$_2$)$_7$CH$_3$)

Deprotection of Alkyne (7) (See FIG. 3).

A 250 ml round bottom flask fitted with a stir bar was charged with 6 (1 eq), potassium carbonate (3 eq), methanol (0.10 M), and tetrahydrofuran (0.17 M). The reaction flask was sealed, then covered with foil to prevent exposure to light and stirred for 3 hr or until complete as indicated by TLC (SiO$_2$: R$_f$=0.4, 10% ethyl acetate/hexanes). The reddish reaction mixture was filtered thru a short silica plug with ethyl acetate, concentrated by rotary evaporation, extracted into ethyl acetate, washed with 1 M HCl and water until neutral, dried over MgSO$_4$, filtered, and then concentrated by rotary evaporation. This crude material was recrystallized from ethanol or isopropanol, filtered via suction filtration and dried under vacuum to give 7 as yellow crystals.

7b, whereby R=—(CH$_2$)$_5$CN: The reagents used: 6b (3.00 g, 6.09 mmol) and potassium carbonate (2.52 g, 18.3 mmol), yielded 7b (2.06 g, 98%). $^1$H NMR (300 MHz, CDCl$_3$): δ 6.92 (s, 2H), 3.98 (t, 4H, J=6.07 Hz), 3.34 (s, 2H), 2.37 (t, 4H, J=6.96 Hz), 1.85-1.63 (m, 12H). $^{13}$C NMR (60 MHz, CDCl$_3$): δ 153.83, 119.56, 117.68, 113.33, 82.76, 79.49, 69.03, 28.18, 25.39, 25.09, 17.08.

7c, whereby R=—(CH$_2$)$_7$CH$_3$: The reagents used: 6c (0.58 g, 1.10 mmol) and potassium carbonate (0.46 g, 3.30 mmol), yielded 7c (0.34 g, 80%). $^1$H NMR (300 MHz, CDCl$_3$): δ 6.93 (s, 2H), 3.95 (t, 4H, J=6.65 Hz), 3.31 (s, 2H), 1.78 (q, 4H, J=7.98 Hz), 1.46-1.39 (m, 4H), 1.30-1.23 (m, 16H), 0.86 (t, 6H, J=6.96 Hz). $^{13}$C NMR (60 MHz, CDCl$_3$): δ 153.93, 117.65, 113.18, 82.38, 79.75, 69.60, 31.78, 29.27, 29.20, 29.09, 25.87, 22.64, 14.10.

(8)

9873-47

Figure 4:
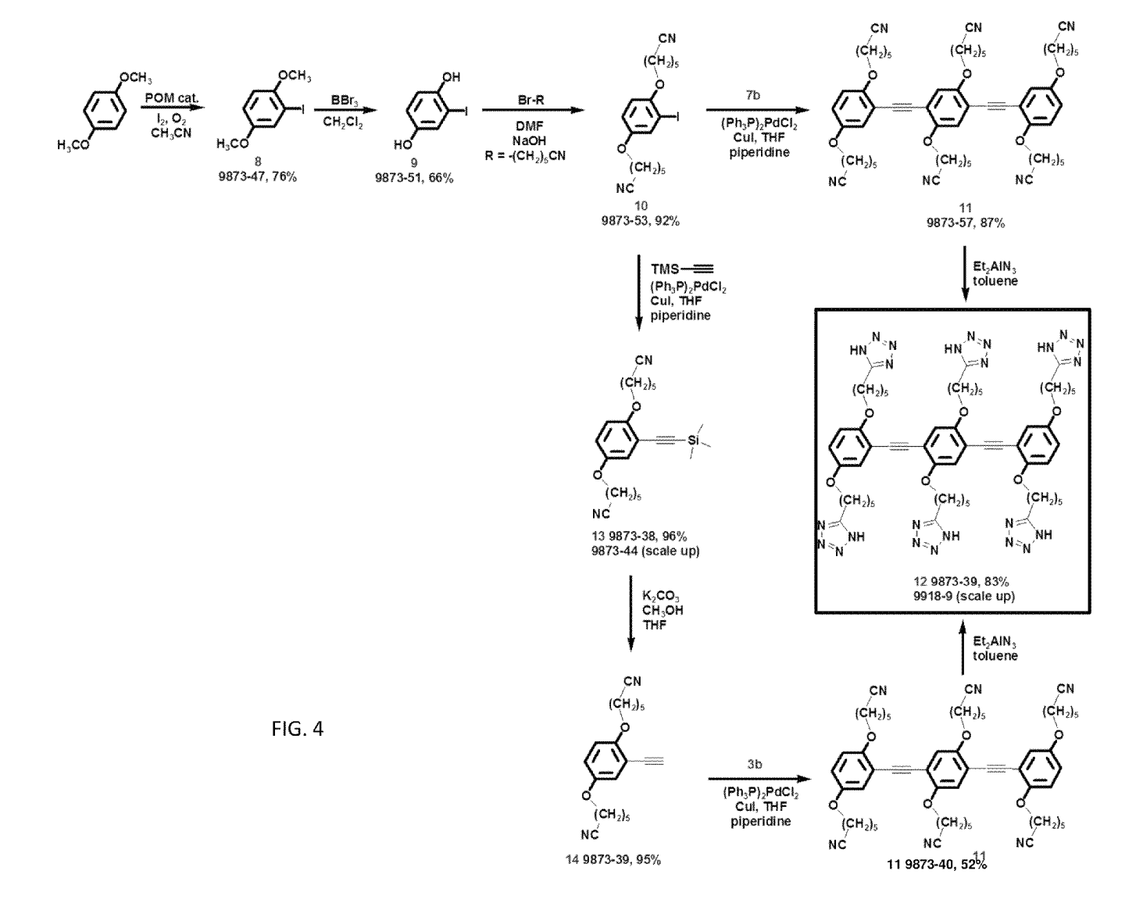
FIG. 4 shows a reaction schematic to form a PPE trimer with six tetrazoles.

Synthesis of 2-iodo-1,4-dimethoxybenzene (8) (See FIG. 4)

Following the procedure from a previous publication (O. V. Branytska et al., *J. Org. Chem.*, 68, 9510-12 (2003)), a 350 ml heavy wall pressure vessel fitted with a stir bar was charged with p-dimethoxybenzene (20.00 g, 144.7 mmol), iodine (18.37 g, 72.37 mmol), oxidation catalyst H$_5$PV$_2$Mo$_{10}$O$_{40}$.34H$_2$O (T. Onoda et al., U.S. Pat. No. 4,146,574 (Mar. 27, 1979)) (3.40 g, 1.45 mmol), and acetonitrile (1.8 M). The vessel was degassed via the freeze-pump-thaw method (2 times) and warmed to room temperature prior to being backfilled with oxygen (2 atm), heated to 80° C., and stirred for 12 hr. The crude reaction mixture was filtered to remove spent catalyst, then water (100 ml) was added and the product extracted into ethyl acetate (100 ml). The organic layer was washed with sodium thiosulfate (aq) and excess water. The organic layer was dried over MgSO$_4$, filtered, and then concentrated by rotary evaporation. Ethanol (100 ml) was added to this crude material in which a white precipitate formed and was filtered via suction filtration yielding 1 as a byproduct. The supernate was concentrated via rotary evaporation and the resulting red oil distilled yielding starting material ~60° C. at 50 mtorr and product 8 (29.2 g, 76%) at ~115° C. at 50 mtorr as a clear oil. $^1$H NMR (300 MHz, CDCl$_3$): δ

7.32 (d, 1H, J=2.94 Hz), 6.84 (dd, 1H, J=5.99 Hz), 6.73 (d, 1H, J=8.95 Hz), 3.81 (s, 3H), 3.73 (s, 3H). $^{13}$C NMR (60 MHz, acetone-d$_6$): δ 154.78, 153.10, 125.09, 115.01, 112.21, 85.95, 56.76, 55.75.

(9)

9873-51

Synthesis of 2-iodo-hydroquinone (9) (See FIG. 4)

Following preparation of 2, a nitrogen purged 500 ml three-neck flask was charged with diiododimethoxy benzene (1) (46.47 g, 176.0 mmol) and stirred until dissolved in methylene chloride (200 ml). The reaction flask was cooled (dry ice/ethanol) and boron tribromide (97.00 g, 387.2 mmol) was added slowly via an addition funnel with the reaction flask vented to a bubblier. The reaction mixture warmed to room temperature and reacted for 17 hr. The pale pink reaction mixture was carefully quenched by pouring into 1 L of chilled water. The white precipitant was collected via suction filtration, washed with excess water until neutral, and dried under vacuum to yield 9 (27.5 g, 66%) which was used without further purification. $^1$H NMR (300 MHz, CDCl$_3$): δ 11.22 (s, 1H), 6.85 (dd, 1H, J=6.27 Hz), 6.74 (dd, 1H, J=5.80 Hz), 4.89 (bs, 1H), 4.48 (bs, 1H). $^{13}$C NMR (60 MHz, DMSO-d$_6$): δ 151.34, 150.06, 125.42, 116.75, 115.64, 83.79.

(10)

9873-53 (R=—(CH$_2$)$_5$CN)

Synthesis of 2-iodo-1,4-diiododialkyoxynitrile Benzene (10) (See FIG. 4)

To a 500 ml schlenk flask under argon fitted with a stir bar was added compound 9 (10.00 g, 42.4 mmol), 6-bromohexanenitrile (15.30 g, 86.9 mmol), and anhydrous DMF (0.5 M). This mixture was deoxygenated via the freeze-pump-thaw method (3 times) then backfilled with argon. Freshly ground sodium hydroxide (6.78 g, 170 mmol) was added and the reaction was stirred at room temperature for 18 hr or until complete as shown by TLC (SiO$_2$: R$_f$=0.3, 30% ethyl acetate/hexanes). To the crude reaction mixture was added 1M HCl, water and ethyl acetate. The crude product was extracted into the organic layer and washed with excess water until reaching a pH of neutral. The organic layer was dried over MgSO$_4$, filtered, and then concentrated by rotary evaporation and further dried under vacuum to yield 10 (16.6 g, 92%) as a reddish oil which was used without further purification. $^1$H NMR (300 MHz, CDCl$_3$): δ 7.28 (s, 1H), 6.80 (dd, 1H, J=6.00 Hz), 6.74 (d, 1H, J=8.96 Hz), 3.95-3.85 (m, 4H), 2.40-2.31 (m, 4H), 1.87-1.54 (m, 6H). $^{13}$C NMR (60 MHz, CDCl$_3$): δ 153.56, 151.93, 125.26, 119.64, 119.55, 115.31, 112.95, 86.83, 69.38, 68.06, 28.40, 28.32, 25.48, 25.29, 25.09, 25.08, 17.14, 17.09.

(11)

9873-57 (R=—(CH$_2$)$_5$CN)

Synthesis of PPE Trimer with Six Nitriles (11) (See FIG. 4)

First option: under argon, a 100 ml schlenk flask fitted with a stir bar was charged with compound 7b (2.44 g, 7.00 mmol), compound 10 (6.12 g, 14.4 mmol), piperidine (0.9 M), and tetrahydrofuran (0.4 M) as a co-solvent. The reaction flask was then deoxygenated via the freeze-pump-thaw method (3 times), backfilled with argon, at which time bis(triphenylphosphine)palladium(II) dichloride (2 mol %) and copper(I) iodide (1 mol %) were added and the vessel sealed and vented to a bubblier. The reaction mixture became heterogeneous and exothermic and stirred at room temperature for 18 hr. The reaction was quenched with the addition of 1N HCl until a neutral pH was detected. The crude product was extracted into ethyl acetate and washed with water and brine. The organic layer was further washed with a 10% ammonium hydroxide (aq) solution to remove spent catalyst salts followed by the addition of 1 N HCl until once again neutral. The organic layer was then dried over MgSO$_4$, filtered, and concentrated by rotary evaporation which produced a dark orange solid. The solid was taken up into ethyl acetate and precipitated out into cold hexanes, filtered via suction filtration, and further dried under vacuum to yield compound 11 (5.78 g, 87%) as a reddish brown powder which was used without further purification.

Second option: under argon, a 100 ml schlenk flask fitted with a stir bar was charged with compound 3b (2.19 g, 3.94 mmol), compound 14 (2.67 g, 8.29 mmol), bis(triphenylphosphine)palladium(II) dichloride (2 mol %), copper(I) iodide (1 mol %), and tetrahydrofuran (0.2 M). The reaction vessel was then sealed, deoxygenated via the freeze-pump-thaw method (3 times), backfilled with argon, and vented to a bubblier. Piperidine (0.7 M), having been deoxygenated using the same method as above, was added to the reaction flask via syringe. The reaction mixture which became heterogeneous and exothermic was stirred at room temperature for 18 hr. The reaction was quenched with the addition of 1N HCl until a neutral pH was detected. The crude product was extracted into ethyl acetate and washed with water and a saturated sodium chloride solution. The organic layer was concentrated by rotary evaporation whereby the dark orange material was filtered through a short silica plug (SiO$_2$: 50% ethyl acetate/hexanes) which produced a dark yellow solid after concentrated by rotary evaporation. The solid was taken up into acetone (10 ml), crashed out into cold ethanol (200 ml), filtered via suction filtration, and further dried under vacuum to yield compound 11 (1.93 g, 52%) which was used without further purification.

$^1$H NMR (300 MHz, acetone-d$_6$): δ 7.10 (s, 2H), 7.02-6.94 (m, 6H), 4.12 (q, 8H, J=6.22 Hz), 4.01 (t, 4H, J=6.26 Hz), 2.53-2.44 (m, 12H), 1.93-1.63 (m, 36H). $^{13}$C NMR (60 MHz, DMSO-d$_6$): δ 153.27, 152.87, 152.25, 120.60, 120.49, 120.46, 118.05, 116.90, 116.75, 114.49, 113.58, 112.74, 91.56, 89.53, 68.69, 67.72, 27.88, 24.73, 24.48, 16.07.

(12)

9873-78 (R=—(CH$_2$)$_5$CN) and 9918-9 (Scale-Up)

Synthesis of PPE Trimer with Six Tetrazoles (12)
(See FIG. 4)

Using glove box techniques, a 500 ml schlenk flask fitted with a stir bar was charged with diethylaluminum chloride (25 wt. % in toluene, 18.4 ml, 33.9 mmol). The sealed schlenk flask was taken out of the glovebox, attached to a schlenk line under argon, and chilled to 0° C. Sodium azide (2.20 g, 33.9 mmol) was then added to the reaction flask, warmed to room temperature, and stirred for 22 hr which produced a cloudy-white mixture. A separate 250 ml schlenk flask under argon also fitted with a stir bar was charged with compound 11 (1:14, ratio of compound 11 to Et$_2$AlN$_3$) (2.00 g, 2.12 mmol) and anhydrous toluene (21 mM) and/or 1-chlorobenzene or 1,2-dichlorobenzene as co-solvent, deoxygenated via the freeze-pump-thaw method (3 times), and backfilled with argon. The diethylaluminum azide mixture was heated to 60° C. and the solution containing compound 11 was warmed to 60° C. then slowly added to the azide mixture via syringe. The reaction flask was sealed and stirred at 85° C. for 20 hr. The reaction flask containing the crude reaction mixture was chilled to 0° C., opened to a schlenk line under argon fitted with a bubblier while a NaOH/NaNO$_2$ solution (3.7 M) was added until a pH of 11 was reached. To this mixture was then added 6 M HCl until a pH of 3 and the product obtained by filtering via suction filtration and washed with excess water. The product was then dried under vacuum and stored in a desiccator to give compound 12 (2.10 g, 83%) as a dark brown powder. $^1$H NMR (300 MHz, DMSO-d$_6$): δ15.5 (bs, tetrazole-H, 6H), 7.05 (s, 2H), 6.99-6.89 (m, 6H), 4.00 (q, 8H, J=6.34 Hz), 3.89 (t, 4H, J=6.34 Hz), 2.90-2.81 (m, 12H), 1.74-1.65 (m, 24H), 1.63-1.37 (m, 12H). $^{13}$C NMR (60 MHz, DMSO-d$_6$): δ 155.95, 153.38, 153.00, 152.38, 118.16, 116.97, 116.95, 114.57, 113.71, 112.88, 91.76, 89.72, 68.82, 67.90, 28.37, 26.82, 25.02, 22.77.

(13)

9873-38 (R=—(CH$_2$)$_5$CN)

Alkyne Coupling Reaction (13) (See FIG. 4).

Under argon, a 200 ml schlenk flask fitted with a stir bar was charged with compound 10 (4.54 g, 10.7 mmol), bis(triphenylphosphine)palladium(II) dichloride (2 mol %), copper(I) iodide (1 mol %), piperidine (1.3 M), and tetrahydrofuran (2.7 M) as co-solvent. The reaction flask was then deoxygenated via the freeze-pump-thaw method (3 times), backfilled with argon, and warmed to room temperature. Trimethylsilylacetylene (1.10 g, 11.2 mmol) was syringed into the flask at which time the reaction mixture became heterogeneous and exothermic. After stirring at room temperature for 3 hr or until completion as shown by TLC (SiO$_2$: R$_f$=0.6, 30% ethyl acetate/hexanes). The dark-brown reaction mixture was filtered thru a short silica plug with ethyl acetate, concentrated by rotary evaporation, extracted into ethyl acetate, washed with 1 M HCl and water until neutral, dried over MgSO$_4$, filtered, and then concentrated by rotary evaporation. This material was dried under vacuum to give 13 (4.06 g, 96%) as a brown powder. $^1$H NMR (300 MHz, CDCl$_3$): δ 6.91 (s, 2H), 6.75 (d, 2H), 3.95 (t, 2H, J=5.94 Hz), 3.87 (t, 2H, J=6.09 Hz), 2.37-2.32 (m, 4H), 1.75-1.68 (m, 12H), 0.22 (s, 9H). $^{13}$C NMR (60 MHz, CDCl$_3$): δ 154.17, 152.36, 119.50, 119.48, 118.59, 116.65, 113.78, 113.21, 101.02, 98.18, 68.74, 67.78, 28.29, 28.27, 25.22, 25.17, 25.00, 24.97, 16.92, 14.02, 0.23.

(14)

9873-39 (R=—(CH$_2$)$_5$CN)

Deprotection of Alkyne (14) (See FIG. 4).

A 500 ml round bottom flask fitted with a stir bar was charged with compound 13 (3.83 g, 9.66 mmol), potassium carbonate (2.00 g, 14.5 mmol), methanol (0.15 M), and tetrahydrofuran (0.21 M). The reaction flask was sealed, then covered with foil to prevent exposure to light and stirred at room temperature for 1.5 hr or until complete as shown by TLC ($SiO_2$: $R_f$=0.4, 10% ethyl acetate/hexanes). The reddish reaction mixture was filtered thru a short silica plug with ethyl acetate, concentrated by rotary evaporation, extracted into ethyl acetate, washed with 1 M HCl and water until neutral, dried over $MgSO_4$, filtered, and then concentrated by rotary evaporation. This material was dried under vacuum to give compound 14 (2.99 g, 95%) as a reddish oil. $^1$H NMR (300 MHz, $CDCl_3$): δ 6.92 (s, 1H), 6.87-6.73 (m, 2H), 3.95 (t, 2H, J=6.09 Hz), 3.86 (t, 2H, J=6.12 Hz), 3.24 (s, 1H), 2.36-2.31 (m, 4H), 1.84-1.51 (m, 12H). $^{13}$C NMR (60 MHz, $CDCl_3$): δ 154.35, 152.43, 119.63, 119.54, 119.14, 116.80, 113.75, 112.30, 81.08, 79.82, 69.00, 67.89, 28.36, 28.21, 25.36, 25.26, 25.07, 25.04, 17.03.

9917-57 Homopolymer (R=—$(CH_2)_5$CN), 9873-22 Copolymer (R=—$(CH_2)_5$CN & R=—$(CH_2)_7CH_3$)

Figure 5:
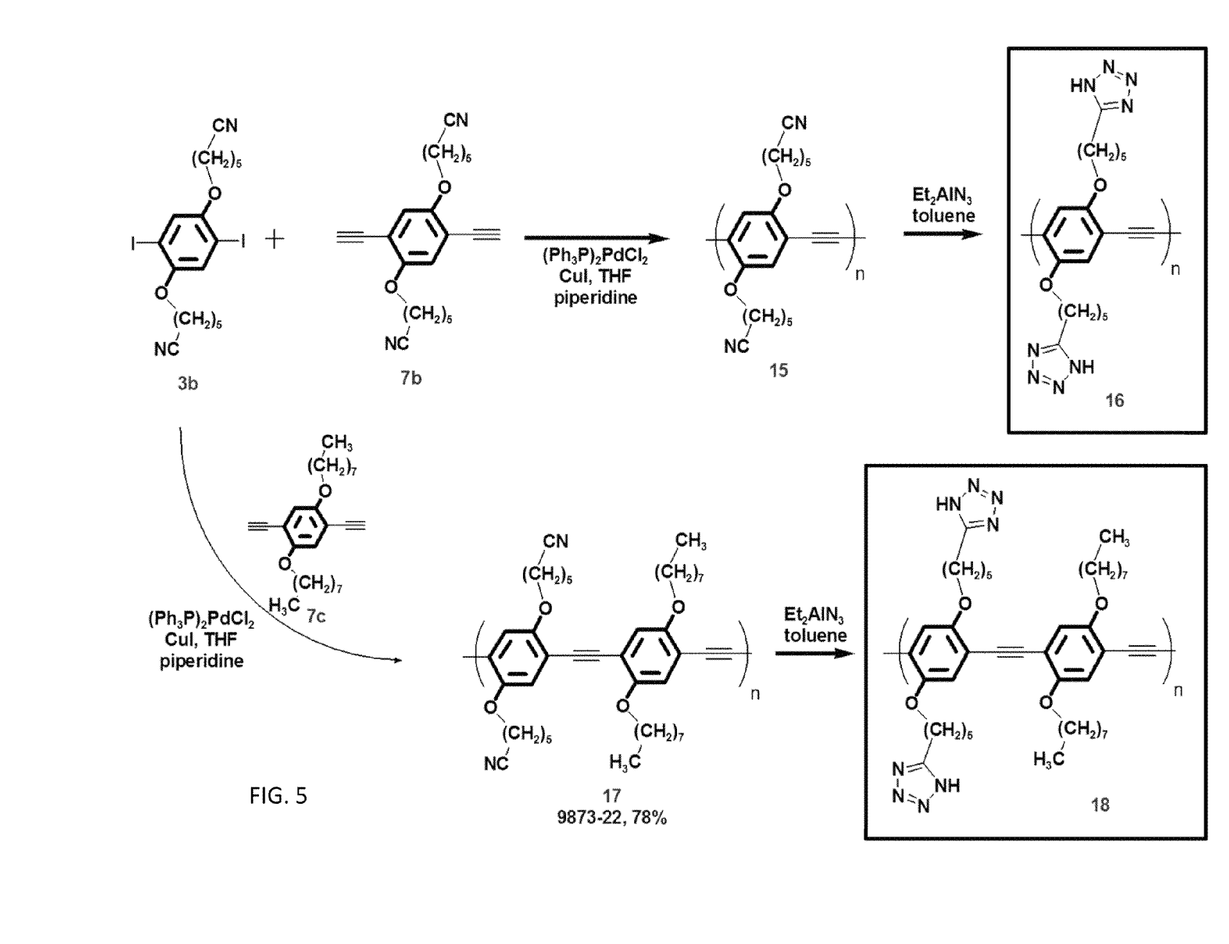
FIG. 5 shows a reaction schematic to form PPE with tetrazoles.

General Procedure for Polymerization (15 & 17) (See FIG. 5).

Under argon, a 100 ml schlenk flask fitted with a stir bar was charged with 3b (1 eq.), a second monomer (1.05 eq; 7b for a homopolymerization or 7c for a copolymerization), bis(triphenylphosphine)palladium(II) dichloride (2 mol %), copper(I) iodide (1 mol %) and tetrahydrofuran (0.18 M). The reaction flask was then deoxygenated via the freeze-pump-thaw method (3 times), backfilled with argon. Piperidine (0.27 M) was added via syringe and the reaction stirred at room temperature for 18 hr. To the reaction mixture was added tetrahydrofuran, chloroform at which time the reaction vessel was heated to 80° C. until most of the material was redissolved. This solution was precipitated into acidic methanol twice, chilled in a freezer overnight, filtered, and dried under vacuum to produce a yellow brown solid as which was used without further purification.

15, whereby R=—$(CH_2)_5$CN: The reagents used: 3b (1.51 g, 2.73 mmol) and 7b (1.00 g, 2.87 mmol), yielded 15 (1.59 g, 90%).

17, whereby (1:1; R=—$(CH_2)_5$CN & R=—$(CH_2)_7CH_3$): The reagents used: 3b (0.89 g, 1.62 mmol) and 7c (0.62 g, 1.62 mmol), yielded 17 (0.86 g, 78%).

Homopolymer 16 (R=—$(CH_2)_5$CN), Copolymer 18 (R=—$(CH_2)_5$CN & R=—$(CH_2)_7CH_3$)

Synthesis of PPE with Tetrazoles (16 & 18) (See FIG. 5)

Figure 6:
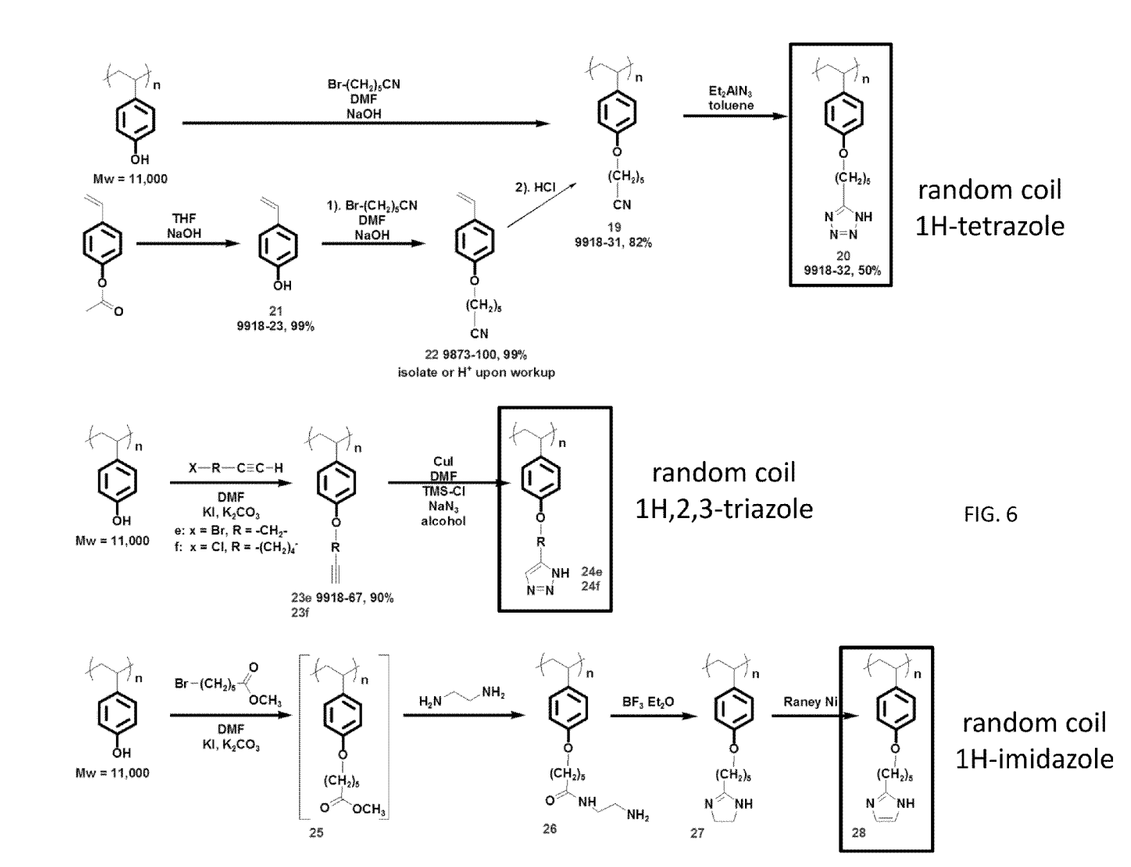
FIG. 6 shows reaction schematics to form a random coil 1H-tetrazole, a random coil 1H,2,3-triazole, and a random coil 1H-imidazole.

Using glove box techniques, a 500 ml schlenk flask fitted with a stir bar was charged with diethylaluminum chloride (25 wt. % in toluene, 18.4 ml, 33.9 mmol). The sealed schlenk flask was taken out of the glovebox, attached to a schlenk line under argon, and chilled to 0° C. Sodium azide (2.20 g, 33.9 mmol) was then added to the reaction flask, warmed to room temperature, and stirred for 22 hr which produced a cloudy-white mixture. A separate 250 ml schlenk flask under argon also fitted with a stir bar was charged with polymer 15 or 17 (1:8, ratio of polymer to $Et_2AlN_3$) (2.00 g, 2.12 mmol) and anhydrous toluene (21 mM) and/or 1-chlorobenzene or 1,2-dichlorobenzene as co-solvent, deoxygenated via the freeze-pump-thaw method (3 times), and backfilled with argon. The diethylaluminum azide mixture was heated to 60° C. and the solution containing polymer 15 or 17 was warmed to 60° C. then slowly added to the azide mixture via syringe. The reaction flask was sealed and stirred at 85° C. for 20 hr. The reaction flask containing the crude reaction mixture was chilled to 0° C., opened to a schlenk line under argon fitted with a bubblier while a NaOH/NaNO$_2$ solution (3.7 M) was added until a pH of 11 was reached. To this mixture was then added 6 M HCl until a pH of 3 and the product obtained by filtering via suction filtration and washed with excess water. The product was then dried under vacuum and stored in a desiccator to give polymer 16 or 18 as a dark brown powder.

then chilled to 0° C., at which time 6 N HCl (aq.) (0.1 ml) was added slowly until a pH of neutral was reached yielding compound 22. Or, with the addition of more acid, in situ-polymerization occurred yielding compound 19. The crude product was extracted into ethyl acetate and washed with water until reaching a pH of neutral. The organic layer was dried over MgSO$_4$, filtered, and then concentrated by rotary evaporation and further dried under vacuum to yield compound 19 (0.61 g, 68%) which was used without further purification. $^1$H NMR (300 MHz, CDCl$_3$): δ 6.65 (br, 4H), 3.87 (br, 2H), 2.35 (br, 2H), 1.69 (br, 7H), 1.25 (br, 2H). $^{13}$C NMR (60 MHz, acetone-d$_6$): δ 157.71, 138.00, 129.08, 120.49, 114.62, 67.88, 41.29, 41.28, 29.15, 25.88, 25.79, 17.

(19)

9918-31 (Option 1: R═—(CH$_2$)$_5$CN), Option 2: 9918-23 to 9873-100 to 9918-31

Synthesis of Compound 19 (See FIG. 6)

Option 1: to a 500 ml schlenk flask under argon fitted with a stir bar was added poly(4-vinylphenol) (Mw~11,000, 5.00 g, 42.0 mmol) and anhydrous DMF (0.8 M). This mixture was deoxygenated via the freeze-pump-thaw method (3 times) then backfilled with argon. Freshly ground sodium hydroxide (6.72 g, 168 mmol) was added and the reaction was stirred at room temperature for 1 hr. After one hour, deoxygenated 6-bromohexanenitrile (8.50 g, 48.3 mmol) was added via syringe and the reaction continued to stir for an additional 48 hr at room temperature. To the crude reaction mixture was added water and ethyl acetate. The crude product was extracted into the organic layer and washed with 1M HCl, brine, and excess water until reaching a pH of neutral. The organic layer was dried over MgSO$_4$, filtered, and then concentrated by rotary evaporation and further dried under vacuum to yield compound 19 (7.90 g, 82%) as a light brown solid which was used without further purification.

Option 2: To a 250 ml round bottom flask under argon and fitted with a stir bar was added 4-acetoxystyrene (15.00 g, 92.6 mmol), tetrahydrofuran (0.97 M), and 5 M solution of sodium hydroxide (aq.) (93 ml), all of which were freshly sparged with argon. The reaction flask was sealed and the reaction was stirred at room temperature for one hour or until the reaction was complete as indicated by TLC (SiO$_2$: R$_f$=0.7, 30% ethyl acetate/hexanes). The crude reaction mixture was chilled to 0° C., at which time 6 N HCl (aq.) (90 ml) was added slowly until a pH of neutral was reached. The product was extracted into ethyl acetate, washed with water three times, dried over MgSO$_4$, filtered, and concentrated by rotary evaporation. Further drying under vacuum yielded 4-vinylphenol 21 (11.72 g, 99%) which was immediately used. A 100 ml schlenk flask under argon was charged with deoxygenated (via the freeze-pump-thaw method, 3 times) t-butanol (0.23 M), 4-vinylphenol 21 (0.50 g, 4.16 mmol), 6-bromohexanenitrile (0.81 g, 4.58 mmol), and potassium t-butoxide (0.56 g, 4.58 mmol). The reaction flask was heated to 97° C. at which time the reaction flask was sealed and the reaction stirred for 18 hours. The crude reaction mixture was (20)

9918-32 (R═—(CH$_2$)$_5$CN)

Synthesis of Compound 20 (See FIG. 6)

Using glove box techniques, a 200 ml schlenk flask fitted with a stir bar was charged with diethylaluminum chloride (25 wt. % in toluene, 7.12 ml, 13.1 mmol). The sealed schlenk flask was taken out of the glovebox, attached to a schlenk line under argon, and chilled to 0° C. Sodium azide (0.85 g, 13.1 mmol) was then added to the reaction flask, warmed to room temperature, and stirred for 3 hr which produced a cloudy-white mixture. A separate 100 ml schlenk flask under argon also fitted with a stir bar was charged with compound 19 (1:3, ratio of compound 19 to Et$_2$AlN$_3$) (1.00 g, 4.36 mmol) and anhydrous toluene (0.2 M) and/or 1-chlorobenzene or 1,2-dichlorobenzene as co-solvent, deoxygenated via the freeze-pump-thaw method (3 times), and backfilled with argon. The diethylaluminum azide mixture was heated to 65° C. and the solution containing compound 19 was warmed to 65° C. then slowly added to the azide mixture via syringe. The reaction flask was sealed and stirred at 65° C. for 36 hr. The reaction flask containing the crude reaction mixture was chilled to 0° C., opened to a schlenk line under argon fitted with a bubblier while a NaOH/NaNO$_2$ solution (3.7 M) was added until a pH of 11 was reached. To this mixture was then added 6 M HCl until a pH of 3 reached. The product was obtained by filtering via gravity filtration and washed with excess water until a pH of neutral. The product was then dried under vacuum and stored in a desiccator to give compound 2 0 (0.59 g, 50%) as a brown powder. $^1$H NMR (300 MHz, DMSO-d$_6$): δ 16.20 (bs, tetrazole-H, 1H), 6.57 (br, 4H), 3.81 (br, 2H), 2.85 (br, 2H), 1.69 (br, 7H), 1.39 (br, 2H). $^{13}$C NMR (60 MHz, DMSO-d$_6$): δ 156.92, 155.86, 137.51, 128.57, 114.26, 67.48, 40.90, 40.85, 28.85, 27.25, 25.50, 23.09.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed as new and desired to be protected by Letters Patent of the United States is:

1. A polymer comprising the formula:

wherein $R_1$ comprises —O—;
wherein $R_2$ comprises any alkyl chain;
wherein $R_3$ comprises —$CH_3$, —CN, —$COOCH_3$, -tetrazole, -imidazole, or -triazole;
wherein $R_4$ comprises —H or —$R_5$;
wherein $R_5$ comprises —H, -halogen, —C≡CH, or —C≡C—; and
wherein n is a positive integer.

2. A co-polymer comprising the formula:

wherein $R_1$ comprises —O—;
wherein $R_2$ comprises any alkyl chain;
wherein $R_3$ comprises —$CH_3$, —CN, —$COOCH_3$, -tetrazole, -imidazole, or -triazole;
wherein n is a positive integer; and
wherein m is a positive integer.

3. A polymer comprising the formula:

4. A method for making the polymer of claim 3, comprising:
(a) reacting 2-iodo-hydroquinone with a haloalkylnitrile, wherein a reaction solvent comprises DMF, t-butanol, or both, wherein a reaction base comprises sodium hydroxide, potassium hydroxide, potassium carbonate, potassium t-butoxide, sodium hydride, or any combination thereof, and wherein the reaction forms 2-iodo-1,4-dialkyoxynitrile benzene;
(b) reacting 2-iodo-1,4-dialkyoxynitrile benzene with wherein R is —$(CH_2)_5CN$), (ii) piperidine, (iii) tetrahydrofuran, (iv) bis(triphenylphosphine)palladium dichloride, and (v) copper iodide to form a PPE polymer with multiple nitriles;
(c) reacting the PPE polymer with (i) toluene, xylene, heptane, hexane, or any combination thereof, (ii) optionally chlorobenzene, 1,2-dichlorobenzene, or both, and (iii) diethylaluminum azide; and
(d) treating the compound formed in step (c) with NaOH/$NaNO_2$ and then with HCl.

5. A polymer comprising the formula:

wherein $R_1$ comprises —O—;
wherein $R_2$ comprises any alkyl chain;

wherein $R_3$ comprises —$CH_3$, —CN, —$COOCH_3$, -tetrazole, -imidazole, or -triazole; and
wherein n is a positive integer.

6. A polymer comprising the formula:

wherein n is a positive integer.

7. A method for making the polymer of claim 6, comprising:
   (a) reacting poly(4-vinylphenol) with a haloalkylnitrile, wherein a reaction solvent comprises DMF, t-butanol, or both, wherein a reaction base comprises sodium hydroxide, potassium hydroxide, potassium carbonate, potassium t-butoxide, sodium hydride, or any combination thereof, and wherein the reaction forms wherein n is a positive integer;

(b) reacting the compound formed in step (a) with (i) toluene, xylene, heptane, hexane, or any combination thereof, (ii) optionally chlorobenzene, 1,2-dichlorobenzene, or both, and (iii) diethylaluminum azide; and
(c) treating the compound formed in step (b) with NaOH/$NaNO_2$ and then with HCl.

8. A method for making the polymer of claim 6, comprising:
   (a) reacting 4-vinyl phenol with a haloalkylnitrile, wherein a reaction solvent comprises DMF, t-butanol, or both, wherein a reaction base comprises sodium hydroxide, potassium hydroxide, potassium carbonate, potassium t-butoxide, sodium hydride or any combination thereof, and wherein the reaction forms wherein $R_1$ comprises —O—, wherein $R_2$ comprises any alkyl chain, and wherein $R_3$ comprises —$CH_3$, —CN, —$COOCH_3$, -tetrazole, -imidazole, or -triazole; and
   (b) reacting the compound formed in step (a) with an acid or initiator for polymerization; and
   (c) reacting the compound formed in step (b) with (i) toluene, xylene, heptane, hexane, or any combination thereof, (ii) optionally chlorobenzene, 1,2-dichlorobenzene, or both, and (iii) diethylaluminum azide.

\* \* \* \* \*